United States Patent
Jung et al.

(10) Patent No.: US 11,380,851 B2
(45) Date of Patent: Jul. 5, 2022

(54) COMPOUND AND ORGANIC LIGHT EMITTING DEVICE COMPRISING THE SAME

(71) Applicant: LG CHEM, LTD., Seoul (KR)

(72) Inventors: Min Woo Jung, Daejeon (KR); Min Young Kang, Daejeon (KR); Tae Yoon Park, Daejeon (KR); Seong Mi Cho, Daejeon (KR); Jeong Wook Mun, Daejeon (KR); Jung Ha Lee, Daejeon (KR); Mi Young Chae, Daejeon (KR)

(73) Assignee: LG CHEM, LTD., Seoul (KR)

( * ) Notice: Subject to any disclaimer, the term of this patent is extended or adjusted under 35 U.S.C. 154(b) by 456 days.

(21) Appl. No.: 16/624,202

(22) PCT Filed: Aug. 31, 2018

(86) PCT No.: PCT/KR2018/010166
§ 371 (c)(1),
(2) Date: Dec. 18, 2019

(87) PCT Pub. No.: WO2019/045528
PCT Pub. Date: Mar. 7, 2019

(65) Prior Publication Data
US 2020/0176689 A1   Jun. 4, 2020

(30) Foreign Application Priority Data

Sep. 1, 2017 (KR) .................. 10-2017-0112077
Aug. 30, 2018 (KR) .................. 10-2018-0102994

(51) Int. Cl.
*H01L 51/00* (2006.01)
*C07D 405/14* (2006.01)
(Continued)

(52) U.S. Cl.
CPC ........ *H01L 51/0072* (2013.01); *C07D 405/14* (2013.01); *C09K 11/06* (2013.01);
(Continued)

(58) Field of Classification Search
CPC ............. H01L 51/0072; H01L 51/0067; H01L 51/0073; H01L 51/5012; H01L 51/5016;
(Continued)

(56) References Cited

U.S. PATENT DOCUMENTS 7,274,141 B2   9/2007   Leo et al.
7,973,203 B2 *  7/2011   Buesing .............. H01L 51/0055
                                                              570/183

(Continued)

FOREIGN PATENT DOCUMENTS

DE    102013208026    11/2013
KR    10-20000051826   8/2000
(Continued)

*Primary Examiner* — Vu A Vu
(74) *Attorney, Agent, or Firm* — Dentons US LLP

(57) ABSTRACT

Provided is a compound of Chemical Formula 1 or 2:

[Chemical Formula 1]

(Continued)

-continued

[Chemical Formula 2]

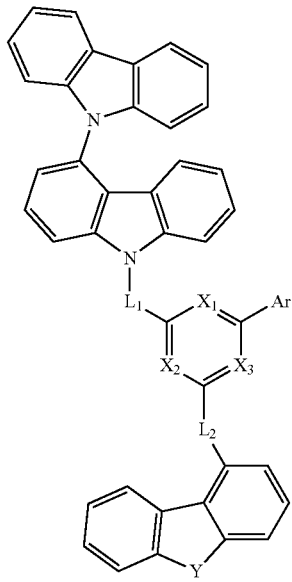

wherein: $X_1$ to $X_3$ are N or CH, with the proviso that at least one of $X_1$ to $X_3$ is N; Y is O or S; $L_1$ and $L_2$ are each independently a single bond or a substituted or unsubstituted $C_{6-60}$ arylene; and Ar is a substituted or unsubstituted $C_{1-60}$ alkyl, a substituted or unsubstituted $C_{1-60}$ haloalkyl, a substituted or unsubstituted $C_{3-60}$ cycloalkyl, a substituted or unsubstituted $C_{6-60}$ aryl, or a substituted or unsubstituted $C_{2-60}$ heteroaryl containing one to three heteroatoms selected from the group consisting of N, O, and S, and an organic light emitting device including the same.

8 Claims, 1 Drawing Sheet

(51) Int. Cl.
  *C09K 11/06* (2006.01)
  *H01L 51/50* (2006.01)
(52) U.S. Cl.
  CPC ...... *H01L 51/0067* (2013.01); *H01L 51/0073* (2013.01); *C09K 2211/1018* (2013.01); *H01L 51/5012* (2013.01); *H01L 51/5016* (2013.01)

(58) Field of Classification Search
  CPC .. C07D 405/14; C07D 209/82; C07D 307/91;
         C09K 11/06; C09K 2211/1018
  USPC ........................................................ 428/690
  See application file for complete search history.

(56) References Cited

U.S. PATENT DOCUMENTS

| | | | |
|---|---|---|---|
| 8,106,391 B2* | 1/2012 | Endo | H01L 51/5048 257/E51.026 |
| 8,580,399 B2 | 11/2013 | Dyatkin et al. | |
| 8,748,015 B2* | 6/2014 | Morishita | H05B 33/14 428/917 |
| 9,831,441 B2* | 11/2017 | Parham | C07D 307/91 |
| 9,966,539 B2* | 5/2018 | Kato | H01L 51/0071 |
| 10,297,755 B2* | 5/2019 | Spencer | H01L 51/0043 |
| 10,600,970 B2* | 3/2020 | Parham | H01L 51/0073 |
| 10,957,859 B2* | 3/2021 | Jatsch | C07D 209/94 |
| 2011/0156016 A1* | 6/2011 | Kawamura | C09K 11/06 252/301.16 |
| 2012/0086329 A1 | 4/2012 | Dyatkin | |
| 2012/0223276 A1 | 9/2012 | Parham et al. | |
| 2012/0259169 A1 | 10/2012 | Merade et al. | |
| 2013/0248845 A1 | 9/2013 | Ogawa et al. | |
| 2013/0293094 A1 | 11/2013 | Dyatkin et al. | |
| 2014/0336379 A1 | 11/2014 | Adachi et al. | |
| 2015/0097176 A1 | 4/2015 | Dyatkin | |
| 2015/0126736 A1 | 5/2015 | Cho et al. | |
| 2015/0266863 A1 | 9/2015 | Dyatkin et al. | |
| 2017/0005276 A1 | 1/2017 | Kim et al. | |
| 2017/0237017 A1 | 8/2017 | Parham et al. | |

FOREIGN PATENT DOCUMENTS

| | | |
|---|---|---|
| KR | 10-20120104246 | 9/2012 |
| KR | 10-20120116282 | 10/2012 |
| KR | 10-20130100330 | 9/2013 |
| KR | 10-20130124217 | 11/2013 |
| KR | 10-20130142967 | 12/2013 |
| KR | 10-20140025445 | 3/2014 |
| KR | 10-20140083898 | 7/2014 |
| KR | 10-20140096182 | 8/2014 |
| KR | 10-20140106631 | 9/2014 |
| KR | 10-20150010387 | 1/2015 |
| KR | 10-20150108332 | 9/2015 |
| KR | 10-20150110101 | 10/2015 |
| KR | 10-20170041886 | 4/2017 |
| KR | 10-20180010808 | 1/2018 |
| WO | 2003012890 | 2/2003 |
| WO | 2012077520 | 6/2012 |
| WO | 2013165192 | 11/2013 |
| WO | 2015009102 | 1/2015 |
| WO | 2018016724 | 1/2018 |

\* cited by examiner

【FIG. 1】
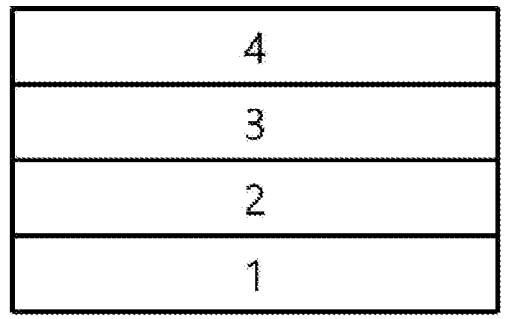
【FIG. 2】
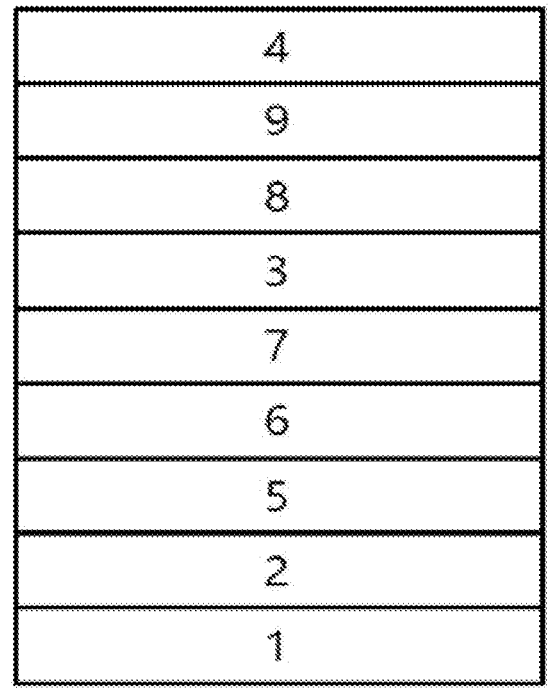

COMPOUND AND ORGANIC LIGHT EMITTING DEVICE COMPRISING THE SAME

CROSS-REFERENCE TO RELATED APPLICATION(S)

This application is a National Stage Application of International Application No. PCT/KR2018/010166 filed on Aug. 31, 2018, which claims the benefit of the filing dates of Korean Patent Application No. 10-2017-0112077 filed with Korean Intellectual Property Office on Sep. 1, 2017, and Korean Patent Application No. 10-2018-0102994 filed with Korean Intellectual Property Office on Aug. 30, 2018, the entire contents of which are incorporated herein by reference.

TECHNICAL FIELD

The present invention relates to a novel compound and to an organic light emitting device including the same.

BACKGROUND

In general, an organic light emitting phenomenon refers to a phenomenon where electrical energy is converted into light energy by using an organic material.

The organic light emitting device using the organic light emitting phenomenon has characteristics such as a wide viewing angle, excellent contrast, a fast response time, and excellent luminance, driving voltage, and response speed, and thus many studies have proceeded thereon.

The organic light emitting device generally has a structure which includes an anode, a cathode, and an organic material layer interposed between the anode and the cathode.

The organic material layer frequently has a multilayered structure that includes different materials in order to enhance efficiency and stability of the organic light emitting device, and for example, the organic material layer can be formed of a hole injection layer, a hole transport layer, a light emitting layer, an electron transport layer, an electron injection layer, and the like.

In the structure of the organic light emitting device, if a voltage is applied between two electrodes, the holes are injected from an anode into the organic material layer and the electrons are injected from the cathode into the organic material layer, and when the injected holes and electrons meet each other, an exciton is formed, and light is emitted when the exciton falls to a ground state again.

There is a continuing need for the development of new materials for the organic materials used in the organic light emitting devices as described above.

PRIOR ART LITERATURE

Patent Literature (Patent Literature 0001) Korean Patent Laid-open Publication No. 10-2000-0051826

DETAILED DESCRIPTION OF THE INVENTION

Technical Problem

It is an object of the present invention to provide a novel compound and an organic light emitting device including the same.

Technical Solution

In one aspect of the invention, there is provided a compound of the following Chemical Formula 1 or 2:

[Chemical Formula 1]

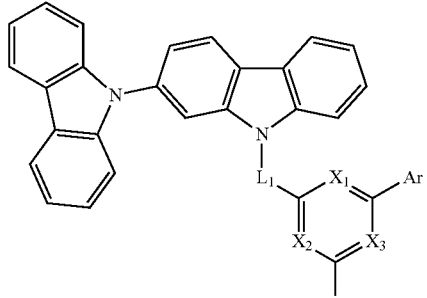

[Chemical Formula 2]

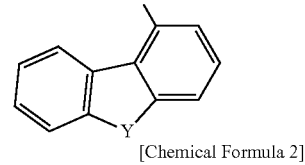
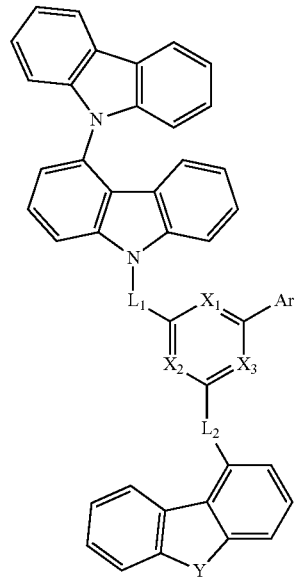

wherein in Chemical Formulas 1 and 2:

$X_1$ to $X_3$ are N or CH, with the proviso that at least one of $X_1$ to $X_3$ is N;

Y is O or S;

$L_1$ and $L_2$ are each independently a single bond or a substituted or unsubstituted $C_{6-60}$ arylene, and Ar is a substituted or unsubstituted $C_{1-60}$ alkyl, a substituted or unsubstituted $C_{1-60}$ haloalkyl, a substituted or unsubstituted $C_{3-60}$ cycloalkyl, a substituted or unsubstituted $C_{6-60}$ aryl, or a substituted or unsubstituted $C_{2-60}$ heteroaryl containing one to three heteroatoms selected from the group consisting of N, O, and S.

In another aspect of the invention, there is provided an organic light emitting device including: a first electrode; a second electrode provided opposite to the first electrode; and one or more organic material layers provided between the first electrode and the second electrode, wherein one or more layers of the organic material layers includes the compound of Chemical Formula 1 or 2.

Advantageous Effects

The compound of Chemical Formula 1 or 2 described above can be used as a material of an organic material layer of an organic light emitting device, and can improve efficiency, achieve a low driving voltage, and/or improve lifetime characteristics in the organic light emitting device.

BRIEF DESCRIPTION OF THE DRAWINGS

FIG. 1 shows an example of an organic light emitting device including a substrate 1, an anode 2, a light emitting layer 3, and a cathode 4.

FIG. 2 shows an example of an organic light emitting device including a substrate 1, an anode 2, a hole injection layer 5, a hole transport layer 6, a light emitting layer 7, an electron transport layer 8, and a cathode 4.

DETAILED DESCRIPTION OF THE EMBODIMENTS

Hereinafter, embodiments of the present invention will be described in more detail to facilitate understanding of the present invention.

As used herein, the notation

means a bond linked to another substituent group, and the single bond means that there is no separate atom present.

As used herein, the term "substituted or unsubstituted" means being unsubstituted or substituted with one or more substituents selected from the group consisting of deuterium, a halogen group, a cyano group, a nitrile group, a nitro group, a hydroxy group, a carbonyl group, an ester group, an imide group, an amino group, a phosphine oxide group, an alkoxy group, an aryloxy group, an alkylthioxy group, an arylthioxy group, an alkylsulfoxy group, an arylsulfoxy group, a silyl group, a boron group, an alkyl group, a cycloalkyl group, an alkenyl group, an aryl group, an aralkyl group, an aralkenyl group, an alkylaryl group, an alkylamine group, an aralkylamine group, a heteroarylamine group, an arylamine group, an arylphosphine group, and a heterocyclic group containing at least one of N, O, and S atoms, or being unsubstituted or substituted with a substituent to which two or more substituents are linked among the substituents exemplified above.

For example, "the substituent to which two or more substituents are linked" can be a biphenyl group.

That is, the biphenyl group can also be an aryl group, and can be interpreted as a substituent to which two phenyl groups are linked.

In the present specification, the number of carbon atoms of a carbonyl group is not particularly limited, but is preferably 1 to 40.

Specifically, the carbonyl group can be a compound having the following structural formulae, but is not limited thereto:

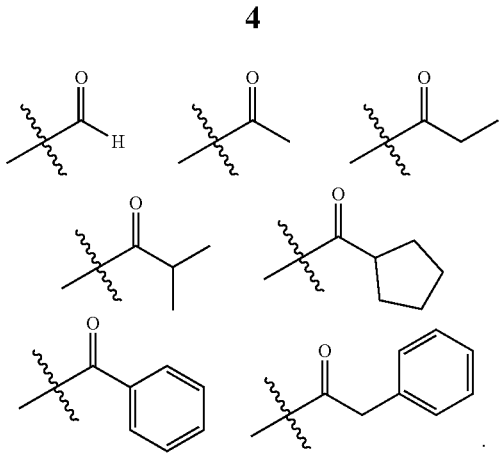

In the present specification, an ester group can have a structure in which oxygen of the ester group can be substituted by a straight-chain, branched-chain, or cyclic alkyl group having 1 to 25 carbon atoms, or an aryl group having 6 to 25 carbon atoms.

Specifically, the ester group can be a compound having the following structural formulae, but is not limited thereto:

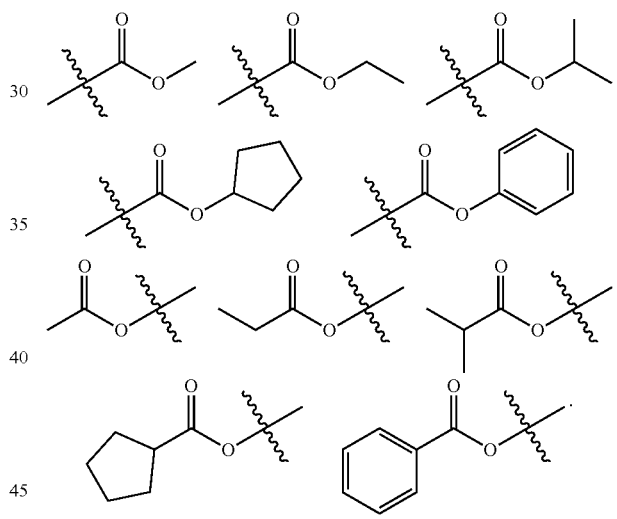

In the present specification, the number of carbon atoms of an imide group is not particularly limited, but is preferably 1 to 25.

Specifically, the imide group can be a compound having the following structural formulae, but is not limited thereto:

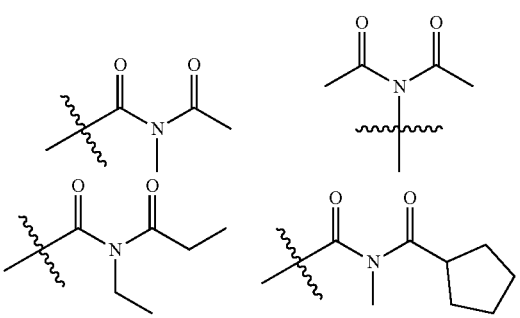

-continued

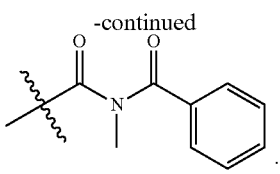

In the present specification, a silyl group specifically includes a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group, and the like, but is not limited thereto.

In the present specification, a boron group specifically includes a trimethylboron group, a triethylboron group, a t-butyldimethylboron group, a triphenylboron group, and a phenylboron group, but is not limited thereto.

In the present specification, examples of a halogen group include fluorine, chlorine, bromine, and iodine.

In the present specification, the alkyl group can be a straight-chain or branched-chain, and the number of carbon atoms thereof is not particularly limited, but is preferably 1 to 40.

According to one embodiment, the number of carbon atoms of the alkyl group is 1 to 20.

According to another embodiment, the number of carbon atoms of the alkyl group is 1 to 10.

According to another embodiment, the number of carbon atoms of the alkyl group is 1 to 6.

Specific examples of the alkyl group include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethyl-butyl, heptyl, n-heptyl, 1-methylhexyl, cyclopentyl-methyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methylhexyl, and the like, but are not limited thereto.

In the present specification, the alkenyl group can be a straight-chain or branched-chain, and the number of carbon atoms thereof is not particularly limited, but is preferably 2 to 40.

According to one embodiment, the number of carbon atoms of the alkenyl group is 2 to 20.

According to another embodiment, the number of carbon atoms of the alkenyl group is 2 to 10.

According to still another embodiment, the number of carbon atoms of the alkenyl group is 2 to 6.

Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenyl-vinyl-1-yl, 2,2-diphenyl-vinyl-1-yl, 2-phenyl-2-(naphthyl-1-yl)vinyl-1-yl, 2,2-bis(diphenyl-1-yl)-vinyl-1-yl, a stilbenyl group, a styrenyl group, and the like, but are not limited thereto.

In the present specification, a cycloalkyl group is not particularly limited, but the number of carbon atoms thereof is preferably 3 to 60. According to one embodiment, the number of carbon atoms of the cycloalkyl group is 3 to 30.

According to another embodiment, the number of carbon atoms of the cycloalkyl group is 3 to 20.

According to still another embodiment, the number of carbon atoms of the cycloalkyl group is 3 to 6.

Specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present specification, an aryl group is not particularly limited, but preferably has 6 to 60 carbon atoms, and can be a monocyclic aryl group or a polycyclic aryl group.

According to one embodiment, the number of carbon atoms of the aryl group is 6 to 30.

According to one embodiment, the number of carbon atoms of the aryl group is 6 to 20.

The aryl group can be a phenyl group, a biphenyl group, a terphenyl group, or the like as the monocyclic aryl group, but is not limited thereto.

The polycyclic aryl group includes a naphthyl group, an anthracenyl group, a phenanthryl group, a pyrenyl group, a perylenyl group, a chrysenyl group, and a fluorenyl group or the like, but is not limited thereto.

In the present specification, a fluorenyl group can be substituted, and two substituent groups can be bonded to each other to form a spiro structure.

In the case where the fluorenyl group is substituted,

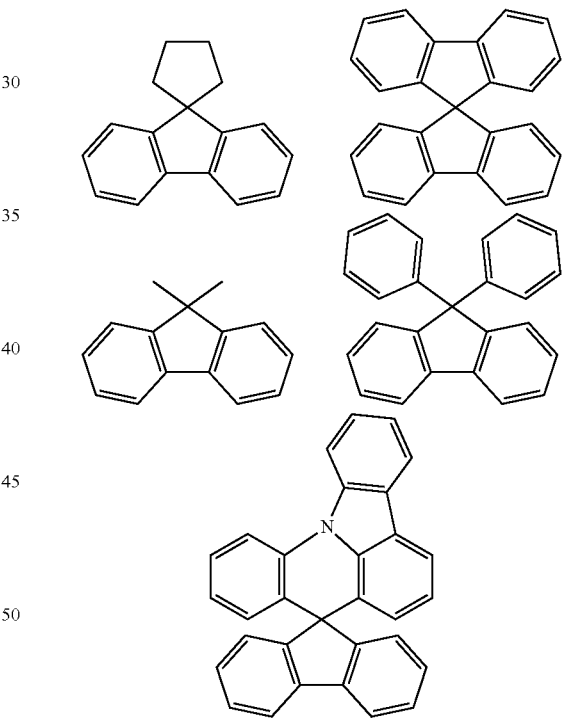

and the like can be formed.

However, the structure is not limited thereto.

In the present specification, a heteroaryl is a heteroaryl including one or more of O, N, Si, and S as a heteroatom, and the number of carbon atoms thereof is not particularly limited, but is preferably 2 to 60.

Examples of the heteroaryl include a thiophene group, a furan group, a pyrrole group, an imidazole group, a thiazole group, an oxazol group, an oxadiazol group, a triazol group, a pyridyl group, a bipyridyl group, a pyrimidyl group, a triazine group, an acridyl group, a pyridazine group, a pyrazinyl group, a quinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzimidazole group, a benzothiazol group, a benzocarbazole group, a benzothiophene group, a dibenzothiophene group, a benzofuranyl group, a phenanthroline group, an isoxazolyl group, a thiadiazolyl group, a phenothiazinyl group, a dibenzofuranyl group, and the like, but are not limited thereto.

In the present specification, the aryl group in the aralkyl group, the aralkenyl group, the alkylaryl group, and the arylamine group is the same as the aforementioned examples of the aryl group.

In the present specification, the alkyl group in the aralkyl group, the alkylaryl group, and the alkylamine group is the same as the aforementioned examples of the alkyl group.

In the present specification, the heteroaryl in the heteroarylamine can be applied to the aforementioned description of the heterocyclic group.

In the present specification, the alkenyl group in the aralkenyl group is the same as the aforementioned examples of the alkenyl group.

In the present specification, the aforementioned description of the aryl group can be applied except that the arylene is a divalent group.

In the present specification, the aforementioned description of the heteroaryl can be applied except that the heteroarylene is a divalent group.

In the present specification, the aforementioned description of the aryl group or cycloalkyl group can be applied except that the hydrocarbon ring is not a monovalent group but is formed by combining two substituent groups.

In the present specification, the aforementioned description of the heteroaryl can be applied, except that the heterocycle is not a monovalent group but is formed by combining two substituent groups.

On the other hand, one embodiment of the present invention provides a compound of Chemical Formula 1 or 2.

Further, $X_1$ to $X_3$ can be N.

Further, $L_1$ and $L_2$ can each independently be a single bond, a substituted or unsubstituted phenylene, a substituted or unsubstituted biphenylylene, a substituted or unsubstituted terphenylylene, a substituted or unsubstituted naphthylene, a substituted or unsubstituted phenanthrenylene, a substituted or unsubstituted anthracenylene, a substituted or unsubstituted fluoranthenylene, a substituted or unsubstituted triphenylenylene, a substituted or unsubstituted pyrenylene, a substituted or unsubstituted carbazolylene, a substituted or unsubstituted fluorenylene, or a substituted or unsubstituted spiro-fluorenylene.

For example, $L_1$ and $L_2$ can each independently be a single bond, phenylene, biphenylylene, or terphenylylene.

Specifically, for example, $L_1$ and $L_2$ can each independently be a single bond or phenylene.

Further, Ar can be a substituted or unsubstituted $C_{6-20}$ aryl, or a substituted or unsubstituted $C_{2-20}$ heteroaryl containing 1 to 3 heteroatoms of O or S.

For example, Ar can be phenyl or biphenyl.

Meanwhile, the aforementioned compound can be any one of the following Chemical Formulas 1-1, 1-2, 2-1, and 2-2:

[Chemical Formula 1-1]

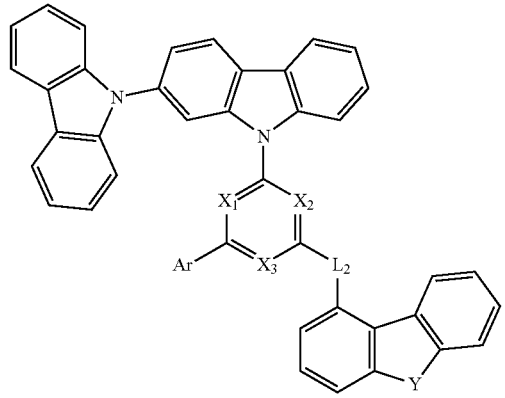

[Chemical Formula 1-2]

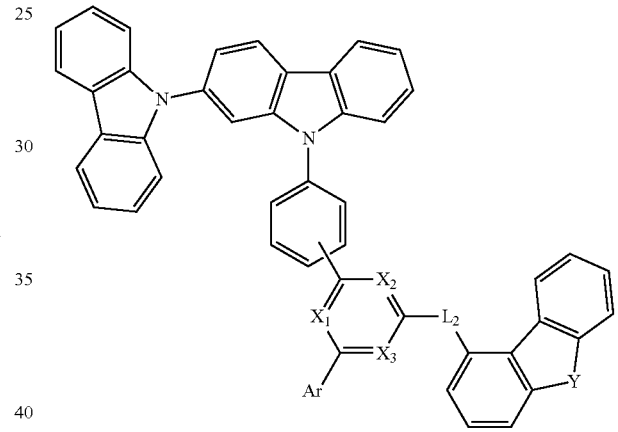

[Chemical Formula 2-1]

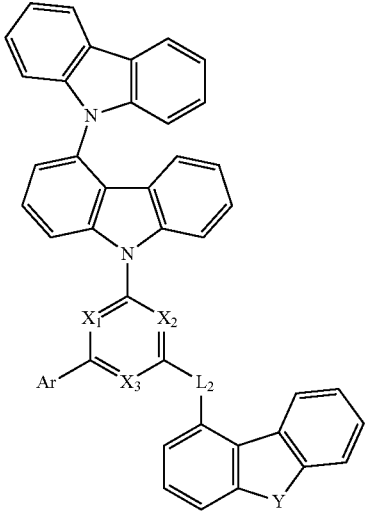

[Chemical Formula 2-2]
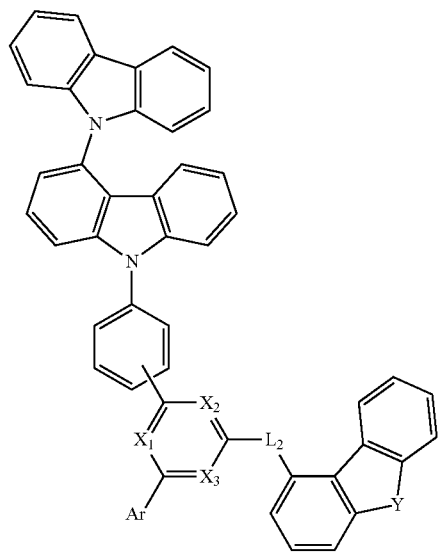
wherein, in Chemical Formulas 1-1, 1-2, 2-1, and 2-2, $X_1$ to $X_3$, Y, $L_2$, and Ar are as defined in Chemical Formulas 1 and 2.
For example, the aforementioned compound can be any one selected from the group consisting of the following compounds:
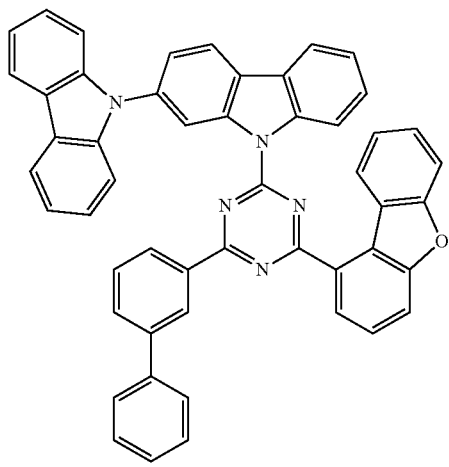
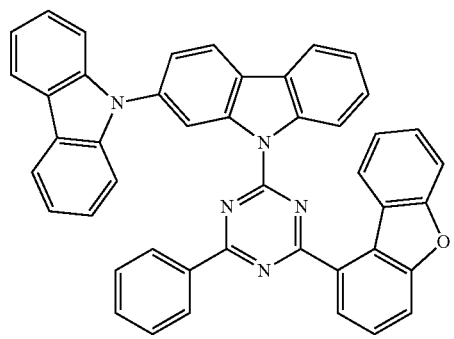
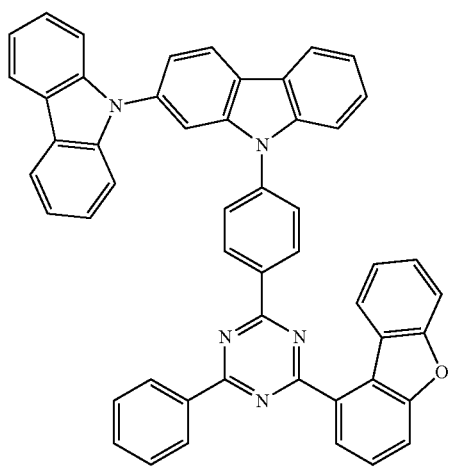
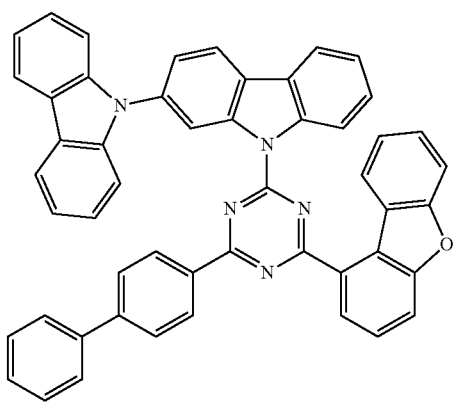
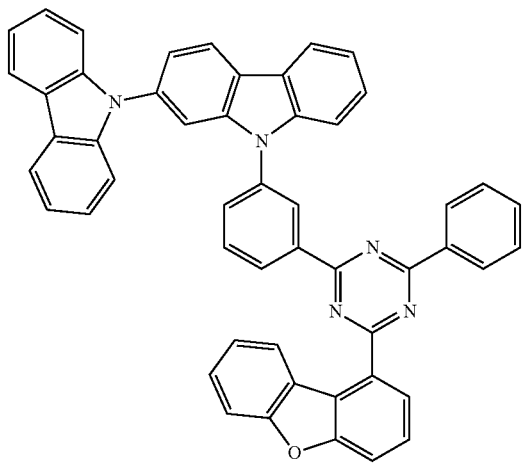

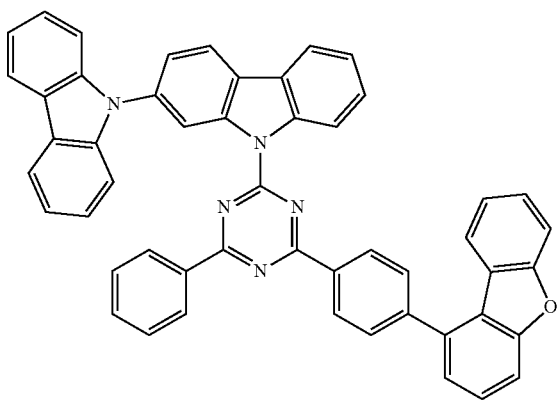

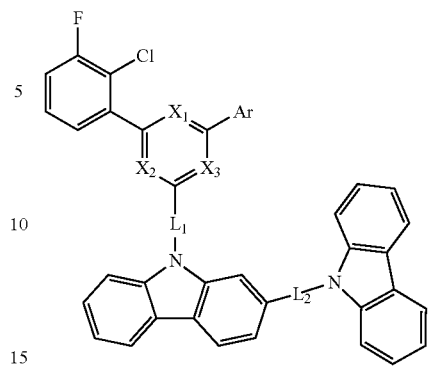

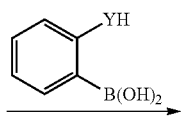

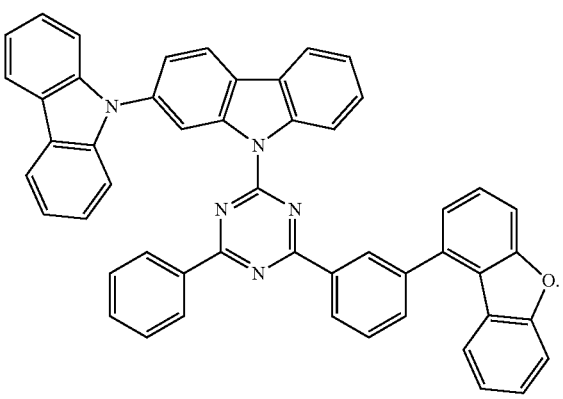

The compounds of Chemical Formulas 1 and 2 have a structure in which a nitrogen-containing 6-membered heteroaryl group is bonded to a biscarbazolyl group bonded to a specific position, and is connected to position 1 of dibenzofuranyl/dibenzothiophenyl. Thus, the organic light emitting device employing these compounds can have high efficiency, a low driving voltage, high luminance, and a long lifetime as compared with an organic light emitting device employing a compound in which an amino group is connected to another position of fluorene.

Meanwhile, the compound of Chemical Formula 1 or 2 can be prepared, for example, according to the preparation method as shown in the following Reaction Scheme a or Reaction Scheme b.

The preparation method can be further specified in preparation examples described hereinafter.

[Reaction Scheme b]

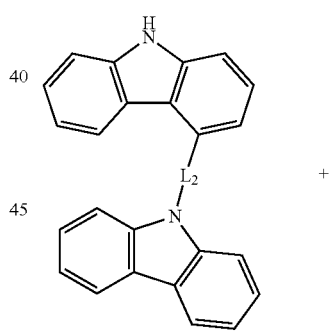

[Reaction Scheme a]

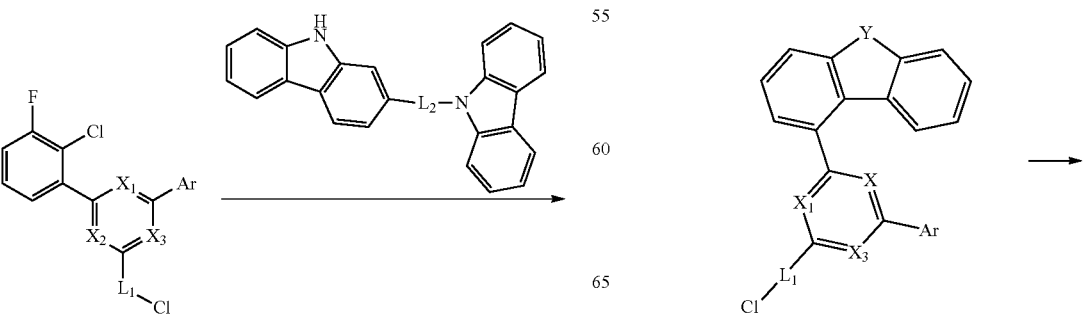

-continued

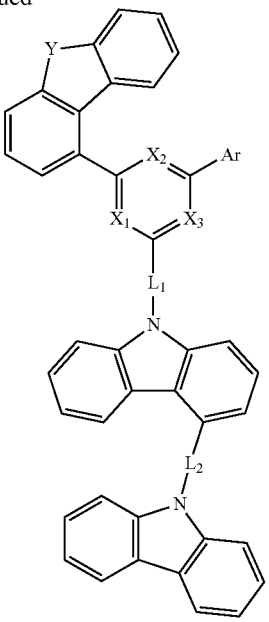

Herein, in Reaction Scheme a or Reaction Scheme b, $X_1$, $X_2$, $X_3$, $Y$, $L_1$, and $L_2$ are as defined above.

The reactants used in Reaction Schemes a and b can be prepared by appropriately replacing the starting materials in compliance with the structure of the compound to be prepared in the present invention.

In another embodiment of the invention, there is provided an organic light emitting device including the compound of Chemical Formula 1 or 2 described above.

As an example, there is provided an organic light emitting device including: a first electrode; a second electrode provided opposite to the first electrode; and one or more organic material layers provided between the first electrode and the second electrode, wherein one or more layers of the organic material layers includes the compound of Chemical Formula 1 or 2.

The organic material layer of the organic light emitting device of the present invention can have a single layer structure, or it can have a multilayered structure in which two or more organic material layers are stacked.

For example, the organic light emitting device of the present invention can have a structure including a hole injection layer, a hole transport layer, a light emitting layer, an electron transport layer, an electron injection layer, and the like as the organic material layer.

However, the structure of the organic light emitting device is not limited thereto, and it can include a smaller number of organic layers.

The organic material layer of the organic light emitting device of the present invention can have a single layer structure, or it can have a multilayered structure in which two or more organic material layers are stacked.

For example, the organic light emitting device of the present invent ion can have a structure further including, as the organic material layer, a hole injection layer and a hole transport layer provided between the first electrode and the light emitting layer, and an electron transport layer and an electron injection layer provided between the light emitting layer and the second electrode, in addition to the light emitting layer.

However, the structure of the organic light emitting device is not limited thereto, and it can include a smaller number of organic layers or a larger number of organic layers.

Further, the organic light emitting device according to the present invention can be a normal type of organic light emitting device in which an anode, one or more organic material layers, and a cathode are sequentially stacked on a substrate.

In addition, the organic light emitting device according to the present invention can be an inverted type of organic light emitting device in which a cathode, one or more organic material layers, and an anode are sequentially stacked on a substrate.

For example, the structure of an organic light emitting device according to an embodiment of the present invention is illustrated in FIGS. 1 and 2.

FIG. 1 shows an example of an organic light emitting device including a substrate 1, an anode 2, a light emitting layer 3, and a cathode 4.

In such a structure, the compound of Chemical Formula 1 or 2 can be included in the light emitting layer.

FIG. 2 shows an example of an organic light emitting device including a substrate 1, an anode 2, a hole injection layer 5, a hole transport layer 6, a light emitting layer 7, an electron transport layer 8, and a cathode 4.

In such a structure, the compound of Chemical Formula 1 or 2 can be included in one or more layers of the hole injection layer, the hole transport layer, the light emitting layer, and the electron transport layer.

The organic light emitting device according to the present invention can be manufactured with materials and methods known in the art, except that one or more layers of the organic material layers include the compound of Chemical Formula 1 or 2.

Moreover, when the organic light emitting device includes a plurality of organic material layers, the organic material layers can be formed of the same material or different materials.

For example, the organic light emitting device according to the present invention can be manufactured by sequentially stacking a first electrode, an organic material layer, and a second electrode on a substrate.

In this case, the organic light emitting device can be manufactured by depositing a metal, metal oxides having conductivity, or an alloy thereof on the substrate using a PVD (physical vapor deposition) method such as a sputtering method or an e-beam evaporation method to form an anode, forming organic material layers including the hole injection layer, the hole transport layer, the light emitting layer, and the electron transport layer thereon, and then depositing a material that can be used as the cathode thereon.

In addition to such a method, the organic light emitting device can be manufactured by sequentially depositing a cathode material, an organic material layer, and an anode material on a substrate.

Further, the compound of Chemical Formula 1 or 2 can be formed into an organic layer by a solution coating method as well as a vacuum deposition method at the time of manufacturing an organic light emitting device.

Herein, the solution coating method means spin coating, dip coating, doctor blading, inkjet printing, screen printing, a spray method, roll coating, or the like, but is not limited thereto.

In addition to such a method, the organic light emitting device can be manufactured by sequentially depositing a cathode material, an organic material layer, and an anode material on a substrate (International Publication WO2003/012890).

However, the manufacturing method is not limited thereto.

As an example, the first electrode is an anode and the second electrode is a cathode, or alternatively, the first electrode is a cathode and the second electrode is an anode.

As the anode material, generally, a material having a large work function is preferably used so that holes can be smoothly injected into the organic material layer.

Specific examples of the anode material include metals such as vanadium, chromium, copper, zinc, and gold, or an alloy thereof; metal oxides such as zinc oxides, indium oxides, indium tin oxides (ITO), and indium zinc oxides (IZO); a combination of metals and oxides, such as ZnO:Al or $SnO_2$:Sb; conductive polymers such as poly(3-methylthiophene), poly[3,4-(ethylene-1,2-dioxy)thiophene] (PEDOT), polypyrrole, and polyaniline, and the like, but are not limited thereto.

As the cathode material, generally, a material having a small work function is preferably used so that electrons can be easily injected into the organic material layer.

Specific examples of the cathode material include metals such as magnesium, calcium, sodium, potassium, titanium, indium, yttrium, lithium, gadolinium, aluminum, silver, tin, and lead, or an alloy thereof; and a multilayered structure material such as LiF/Al, $LiO_2$/Al, and the like, but are not limited thereto.

The hole injection layer is a layer for injecting holes from the electrode, and the hole injection material is preferably a compound which has a capability of transporting the holes, thus has a hole injecting effect in the anode and an excellent hole injecting effect to the light emitting layer or the light emitting material, prevents excitons produced in the light emitting layer from moving to the electron injection layer or the electron injection material, and is excellent in the ability to form a thin film.

It is preferable that a HOMO (highest occupied molecular orbital) of the hole injection material is between the work function of the anode material and a work function of a peripheral organic material layer.

Specific examples of the hole injection material include metal porphyrine, oligothiophene, an arylamine-based organic material, a hexanitrilehexaaza-triphenylene-based organic material, a quinacridone-based organic material, a perylene-based organic material, anthraquinone, polyaniline, and a polythiophene-based conductive polymer, and the like, but are not limited thereto.

The hole transport layer is a layer that receives holes from a hole injection layer and transports the holes to the light emitting layer. The hole transport material is suitably a material having large mobility to the holes, which can receive holes from the anode or the hole injection layer and transfer the holes to the light emitting layer.

Specific examples thereof include an arylamine-based organic material, a conductive polymer, a block copolymer in which a conjugate portion and a non-conjugate portion are present together, and the like, but are not limited thereto.

The light emitting material is preferably a material which can receive holes and electrons transported from a hole transport layer and an electron transport layer, respectively, combine the holes and the electrons to emit light in a visible ray region, and has good quantum efficiency to fluorescence or phosphorescence.

Specific examples of the light emitting material include an 8-hydroxy-quinoline aluminum complex ($Alq_3$), a carbazole-based compound, a dimerized styryl compound, BAlq, a 10-hydroxybenzoquinoline-metal compound, a benzoxazole compound, benzothiazole compound, a benzimidazole-based compound, a poly(p-phenylene vinylene) (PPV)-based polymer, a spiro compound, polyfluorene, rubrene, and the like, but are not limited thereto.

The light emitting layer can include a host material and a dopant material.

The host material can be a fused aromatic ring derivative, a heterocycle-containing compound, or the like.

Specific examples of the fused aromatic ring derivatives include anthracene derivatives, pyrene derivatives, naphthalene derivatives, pentacene derivatives, phenanthrene compounds, fluoranthene compounds, and the like. Examples of the heterocyclic-containing compounds include carbazole derivatives, dibenzofuran derivatives, ladder-type furan compounds, pyrimidine derivatives, and the like, but are not limited thereto.

The dopant material includes an aromatic amine derivative, a styrylamine compound, a boron complex, a fluoranthene compound, a metal complex, and the like.

Specifically, the aromatic amine derivative is a substituted or unsubstituted fused, aromatic ring derivative having an arylamino group, and examples thereof include pyrene, anthracene, chrysene, periflanthene, and the like, which have an arylamino group. The stearylamine compound is a compound where at least one arylvinyl group is substituted in a substituted or unsubstituted arylamine, in which one or two or more substituent groups selected from the group consisting of an aryl group, a silyl group, an alkyl group, a cycloalkyl group, and an arylamino group are substituted or unsubstituted.

Specific examples thereof include styrylamine, styryldiamine, styryltriamine, styryltetramine, and the like, but are not limited thereto.

Further, the metal complex includes an iridium complex, a platinum complex, and the like, but is not limited thereto.

The electron transport layer is a layer which receives electrons from an electron injection layer and transports the electrons to a light emitting layer, and an electron transport material is suitably a material which can receive electrons well from a cathode and transfer the electrons to a light emitting layer, and has large mobility for electrons.

Specific examples thereof include an Al complex of 8-hydroxyquinoline, a complex including $Alq_3$, an organic radical compound, a hydroxyflavone-metal complex, and the like, but are not limited thereto.

The electron transport layer can be used with any desired cathode material, as used according to the related art.

In particular, appropriate examples of the cathode material are a typical material which has a low work function, followed by an aluminum layer or a silver layer.

Specific examples thereof include cesium, barium, calcium, ytterbium, and samarium, in each case followed by an aluminum layer or a silver layer.

The electron injection layer is a layer which injects electrons from an electrode, and is preferably a compound which has a capability of transporting electrons, has an effect of injecting electrons from a cathode and an excellent effect of injecting electrons into a light emitting layer or a light emitting material, prevents excitons produced from the light emitting layer from moving to a hole injection layer, and is also excellent in the ability to form a thin film.

Specific examples thereof include fluorenone, anthraquinodimethane, diphenoquinone, thiopyran dioxide, oxazole, oxadiazole, triazole, imidazole, perylenetetracarboxylic acid, fluorenylidene methane, anthrone, and the like, and derivatives thereof, a metal complex compound, a nitrogen-containing 5-membered ring derivative, and the like, but are not limited thereto.

Examples of the metal complex compound include 8-hydroxyquinolinato lithium, bis(8-hydroxyquinolinato)-zinc, bis(8-hydroxyquinolinato)copper, bis(8-hydroxyquinolinato)manganese, tris(8-hydroxyquinolinato)-aluminum, tris(2-methyl-8-hydroxyquinolinato)aluminum, tris(8-hydroxyquinolinato)gallium, bis(10-hydroxybenzo[h]quinolinato) beryllium, bis(10-hydroxybenzo[h]-quinolinato)zinc, bis(2-methyl-8-quinolinato)-chloro-gallium, bis(2-methyl-8-quinolinato) (o-cresolato)-gallium, bis(2-methyl-8-quinolinato) (1-naphtholato)-aluminum, bis(2-methyl-8-quinolinato) (2-naphtholato)-gallium, and the like, but are not limited thereto.

The organic light emitting device according to the present invention can be a front side emission type, a back side emission type, or a double-sided emission type according to the used material.

In addition, the compound of Chemical Formula 1 or 2 can be included in an organic solar cell or an organic transistor in addition to an organic light emitting device.

The preparation of the compound of Chemical Formula 1 or 2 and the organic light emitting device containing the same will be described in detail in the following examples.

However, these examples are presented for illustrative purposes only, and are not intended to limit the scope of the present invention.

<Preparation Example 1> Preparation of Compound A

The reaction product was cooled and distilled, and the resultant solid was washed with diethyl ether and dried to prepare Compound A-1.

(22.1 g, yield: 91%)

Preparation of Compound A-2

Dimethylamine (2.0 M solution) (74.8 mL, 150 mmol) and triethylamine (37.9 mL, 272 mmol) were added to diethyl ether (500 mL) and then Compound A-1 (27 g, 140 mmol) was slowly added dropwise and stirred for 30 minutes.

The resultant solid was filtered and then the filtrate was distilled to prepare Compound A-2.

(23.4 g, yield: 83%)

Preparation of Compound A

N'-cyanobenzimidamide (16.8 g, 114 mmol), Compound A-2 (23 g, 114 mmol), and phosphorus oxychloride (12 mL, 128 mmol) were added to 500 mL of acetonitrile, and then the mixture was stirred and refluxed for 1 hour.

The reaction product was cooled to room temperature, and then the resultant solid was washed with water and ethanol and then dried to prepare Compound A.

(29.2 g, yield: 80%)

<Preparation Example 2> Preparation of Compound 1

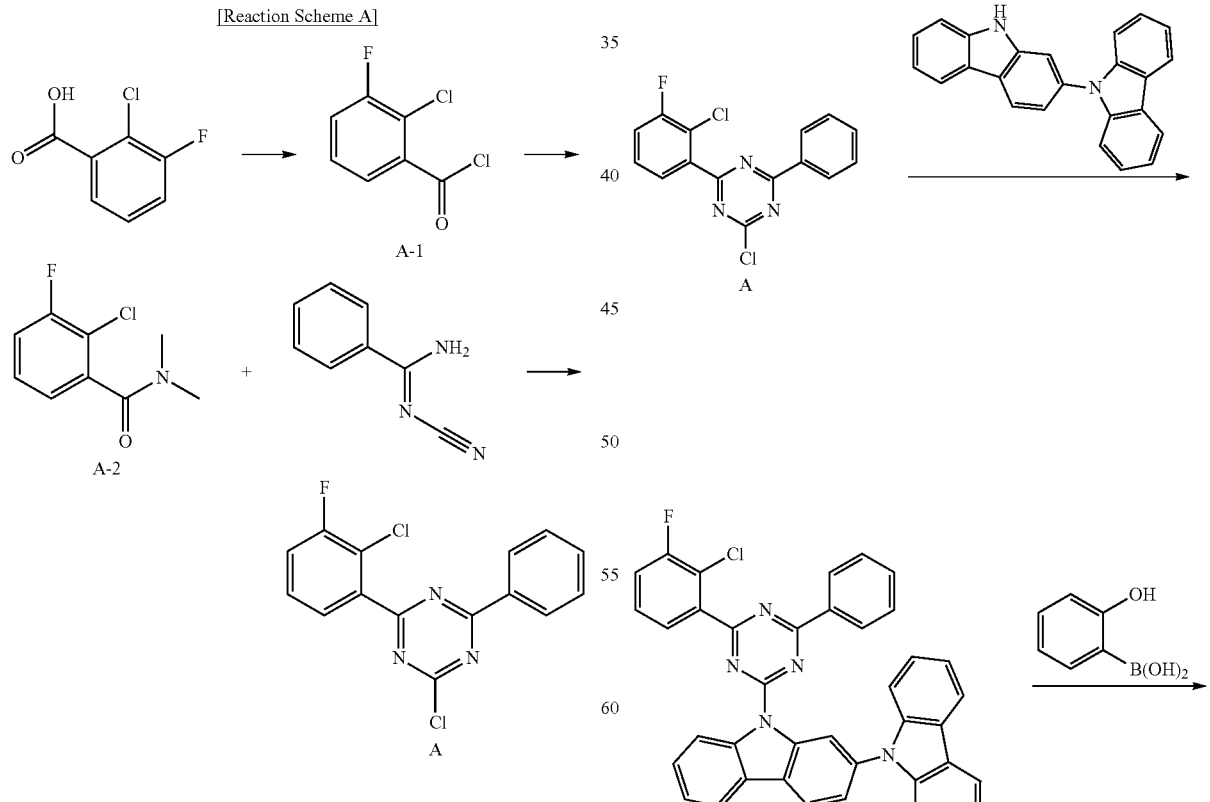

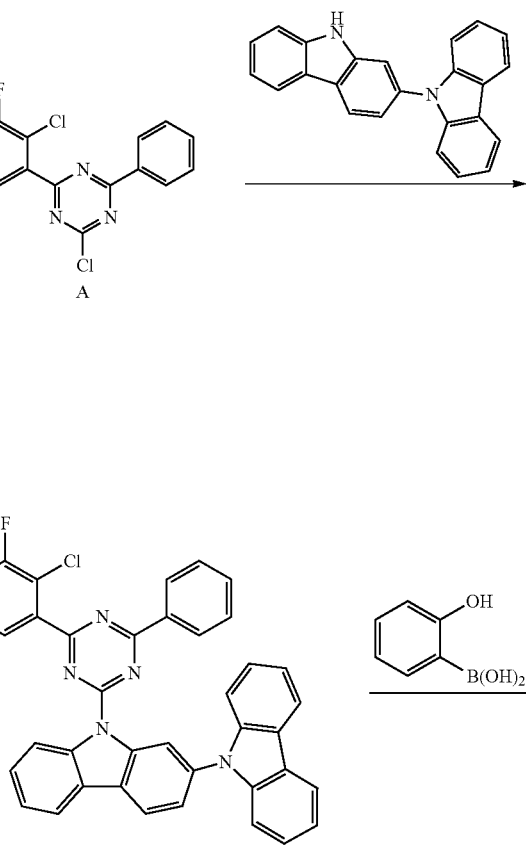

Preparation of Compound A-1

2-chloro-3-fluorobenzoic acid (22 g, 126 mmol) was added to thionyl chloride (200 mL), and then the mixture was stirred under reflux for 2 hours.

-continued

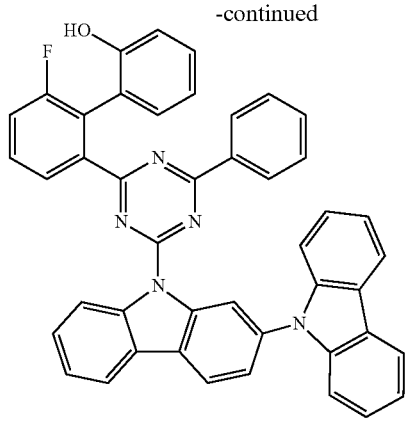

1-2

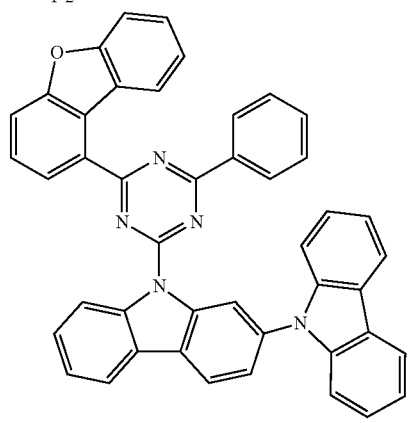

1

Preparation of Compound 1-1

Compound A (20 g, 62 mmol) and 9H-2,9'-bicarbazole (21 g, 62 mmol) were dispersed in 100 mL of toluene, and sodium tert-butoxide (12 g, 125 mmol) was added thereto and heated.

Bis(tri-tert-butylphosphine)palladium (0.32 g, 1 mol %) was added under reflux and reacted for 6 hours.

After completion of the reaction, the reaction mixture was cooled to room temperature, and the resultant solid was filtered.

The filtered solid was dissolved in chloroform again, anhydrous magnesium sulfate was added thereto, and the mixture was stirred, then filtered, and distilled under reduced pressure.

The product was recrystallized with chloroform and ethyl acetate to prepare Compound 1-1.

(26.9 g, yield: 70%)

Preparation of Compound 1-2

Compound 1-1 (20 g, 32.5 mmol) and Compound (2-hydroxyphenyl)boronic acid (4.5 g, 32.5 mmol) were dispersed in 90 mL of 1,4-dioxane, and potassium phosphate (13.8 g, 65 mmol) and water (30 mL) were further added thereto.

Dibenzylideneacetone palladium (0.56 g, 3 mol %) and tricyclohexylphosphine (0.55 g, 6 mol %) were added under refluxing and stirring conditions, and the mixture was stirred at reflux for 12 hours.

After completion of the reaction, the mixture was cooled to room temperature, and the aqueous layer was separated and concentrated under reduced pressure. Then, chloroform was added to the residue, and the mixture was dissolved and washed with water to separate the organic layer.

The separated organic layer was dried over anhydrous magnesium sulfate and filtered.

To the compound obtained by concentration under reduced pressure, ethanol and ethyl acetate were added to form a slurry, and the solid was filtered to prepare Compound 1-2.

(16.0 g, yield: 73%)

Preparation of Compound 1

Compound 1-2 (20 g, 30 mmol) was added to 100 ml of dimethylforamide and stirred.

Then, potassium carbonate (8.2 g, 60 mmol) was added and refluxed.

After 2 hours, the reaction mixture was cooled to room temperature and filtered.

The filtrate was poured into excess water to precipitate a solid, which was filtered.

The filtered solid was dissolved in chloroform again, washed twice with water, and separated.

The combined organic layers were dried over magnesium sulfate.

While removing chloroform under reflux, ethyl acid was added and recrystallized to prepare Compound 1.

(13.2 g, yield: 68%; MS: [M+H]$^+$=654)

<Preparation Example 3> Preparation of Compound 2

[Reaction Scheme 2]

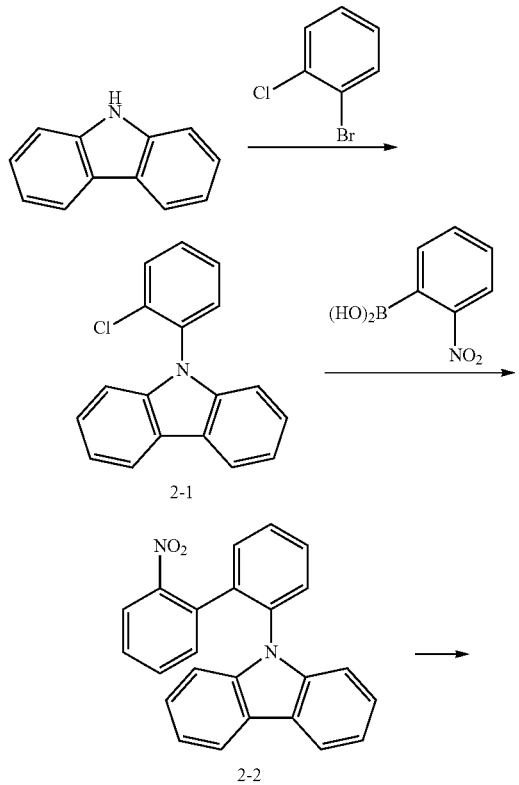

-continued

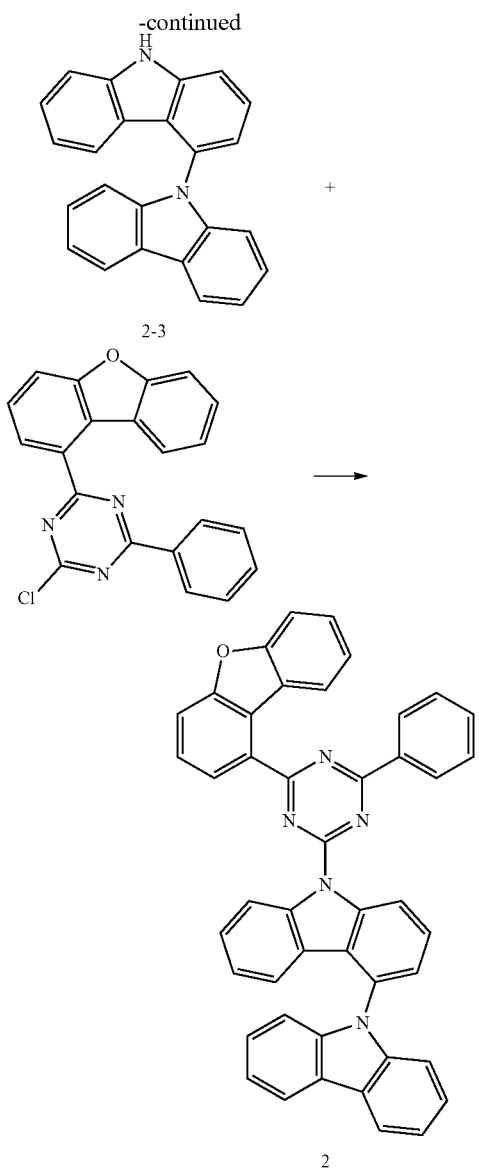

Preparation of Compound 2-1

9H-carbazole (25 g, 150 mmol) and Compound 1-bromo-2-chlorobenzene (28.6 g, 150 mmol) were dispersed in 250 mL of toluene, and sodium tert-butoxide (28.7 g, 300 mmol) was added and heated.

Bis(tri-tert-butylphosphine)palladium (760 mg, mol %) was added under reflux, and reacted for 6 hours.

After completion of the reaction, the reaction mixture was cooled to room temperature and washed twice with water. The organic layer was separated and anhydrous magnesium sulfate was added thereto, and the mixture was stirred, filtered, and concentrated under reduced pressure.

The concentrated compound was slurried with ethanol and ethyl acetate to prepare Compound 2-1.

(31.6 g, yield: 76%)

Preparation of Compound 2-2

Compound 1 (25 g, 90 mmol) and Compound (2-nitrophenyl) boronic acid (15.0 g, 90 mmol) were dispersed in 180 mL of 1,4-dioxane, and potassium phosphate (38.2 g, 180 mmol) and water (50 mL) were further added thereto.

Dibenzylideneacetone palladium (1.5 g, 3 mol %) and tricyclohexylphosphine (1.5 g, 6 mol %) were added under refluxing and stirring conditions, and the mixture was stirred at reflux for 12 hours.

After completion of the reaction, the mixture was cooled to room temperature, and the aqueous layer was separated and concentrated under reduced pressure. Then, chloroform was added to the residue, and the mixture was dissolved and washed with water to separate the organic layer.

The separated organic layer was dried over anhydrous magnesium sulfate and filtered.

To the compound obtained by concentration under reduced pressure, ethyl acetate was added to form a slurry, and the solid was filtered to prepare Compound 2-2.

(26.5 g, yield: 81%)

Preparation of Compound 2-3

Triethyl phosphite (P(OEt)$_3$) (10.9 g, 65.9 mmol) was added to Compound 2-2 (20 g, 55 mmol), and the mixture was heated and stirred.

When the reaction was completed, the remaining triethyl phosphite was distilled off under vacuum, and the mixture was cooled to room temperature and stirred.

Hexane and ethyl acetate were added thereto, the resultant solid was filtered, and the filtered solid was washed with hexane.

The solid was again dissolved in chloroform, washed twice with water, and separated. Anhydrous magnesium sulfate was added to the organic layer, slurried, filtered, and concentrated under reduced pressure.

The compound was purified through a silica column using hexane and ethyl acetate to prepare Compound 2-3.

(13.6 g, yield: 75%)

Preparation of Compound 2

Compound 2 was prepared in the same manner as in Preparation Example of Compound 2-1 by using Compound 2-3 (20 g, 60 mmol) and Compound 2-chloro-4-(dibenzo[b,d]furan-1-yl)-6-phenyl-1,3,5-triazine (21.5 g, 60 mmol).

(29.9 g, yield: 76%: MS: [M+H]$^+$=654)

<Preparation Example 4> Preparation of Compound 3

[Reaction Scheme 3]

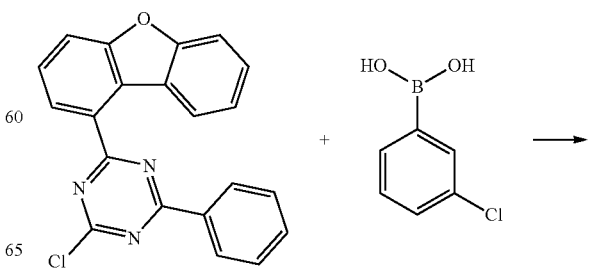

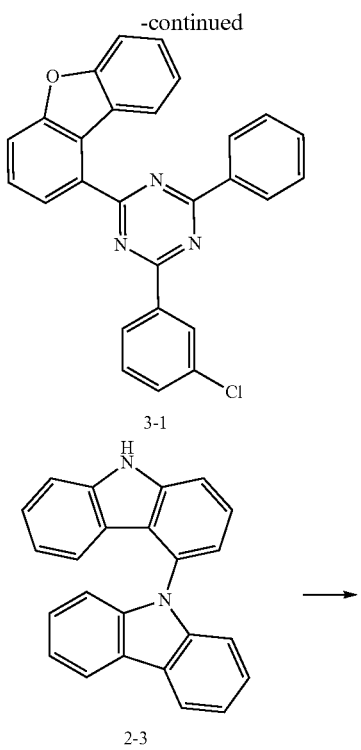

Preparation of Compound 3-1

Compound 2-chloro-4-(dibenzo[b,d]furan-1-yl)-6-phenyl-1,3,5-triazine (50.0 g, 140 mmol) and Compound (3-chlorophenyl)boronic acid (24 g, 154 mmol) were dispersed in 90 mL of 1,4-dioxane, and potassium carbonate (58.1 g, 420 mmol) and water (120 mL) were further added thereto.

Tetratriphenylphosphine palladium(0) (4.9 g, 3 mol %) was added under refluxing and stirring conditions, and the mixture was stirred at reflux for 4 hours.

After completion of the reaction, the mixture was cooled to room temperature, and the solid was filtered. Then, chloroform was added thereto and the mixture was washed with water to separate the organic layer.

The separated organic layer was dried over anhydrous magnesium sulfate and filtered.

To the compound obtained by concentration under reduced pressure, ethanol and ethyl acetate were added and slurried to prepare Compound 3-1.

(35 g, yield: 57%)

Preparation of Compound 3

Compound 2-3 (20 g, 60.22 mmol) and Compound 3-1 (28.7 g, 32 mmol) were dissolved in 200 mL of xylene, and then sodium tert-butoxide (12 g, 120 mmol) was added thereto and heated.

Bis(tri-tert-butylphosphine)palladium (0.9 g, 3 mol %) was added thereto, and the mixture was stirred and refluxed for 12 hours.

When the reaction was completed, the temperature was lowered to room temperature, and the resultant solid was filtered.

The filtered solid was dissolved in chloroform, washed twice with water, and the organic layer was separated, then anhydrous magnesium sulfate was added thereto, stirred, and filtered. The filtrate was distilled under reduced pressure.

The concentrate was purified through a silica column using chloroform and hexane to prepare Compound 3 (18 g, 41%, MS: [M+H]$^+$=730) as a white solid compound.

EXAMPLES

Example 1

A glass substrate thinly coated with ITO (indium tin oxide) to a thickness of 1300 Å was put into distilled water in which a detergent was dissolved, and ultrasonically cleaned.

In this case, a product manufactured by Fischer Co. was used as the detergent, and as the distilled water, distilled water filtered twice using a filter manufactured by Millipore Co. was used.

After the ITO was cleaned for 30 minutes, ultrasonic cleaning was repeated twice using distilled water for 10 minutes.

After the cleaning with distilled water was completed, the substrate was ultrasonically cleaned with solvents of isopropyl alcohol, acetone, and methanol, then dried and transferred to a plasma cleaner.

In addition, the substrate was cleaned for 5 minutes using oxygen plasma, and then transferred to a vacuum depositor.

On the ITO transparent electrode thus prepared, the following compound HI-1 was thermally vacuum deposited to a thickness of 50 Å to form a hole injection layer.

The following compound HT-1 was thermally vacuum deposited on the hole injection layer to a thickness of 250 Å to form a hole transport layer, and the following compound HT-2 was vacuum deposited on the HT-1 deposited film to a thickness of 50 Å to form an electron blocking layer.

Next, on the HT-2 deposited film, Compound 1 synthesized in Preparation Example 2 was vacuum-deposited at 90 wt % as a phosphorescent host and the phosphorescent dopant GD-1 was vacuum-deposited at 10 wt %, thereby forming a light emitting layer with a thickness of 300 Å.

An ET-1 material was vacuum deposited on the light emitting layer to a thickness of 250 Å, and an ET-2 material was further co-deposited with 2 wt % of Li to a thickness of 100 Å to form an electron transport layer and an electron injection layer.

Aluminum was deposited on the electron injection layer to a thickness of 1000 Å to form a cathode.

In the above-mentioned process, the vapor deposition rate of the organic material was maintained at 0.4 to 0.7 Å/s, the deposition rates of aluminum was maintained at 2 Å/s, and the degree of vacuum during the deposition was maintained at $1\times10^{-7}$ to $5\times10^{-8}$ Torr.

Example 2

A device of Example 2 was manufactured in the same manner as in Example 1, except that Compound 2 was used instead of Compound 1 in Example 1.

Example 3

A device of Example 3 was manufactured in the same manner as in Example 1, except that Compound 3 was used instead of Compound 1 in Example 1.

COMPARATIVE EXAMPLES

Comparative Examples 1 to 3

Devices of comparative examples were manufactured in the same manner as in Example 1, except that Compounds A to C were used instead of Compound 1 in Example 1.

In this case, the host material compounds A to C used in the comparative examples are as follows.

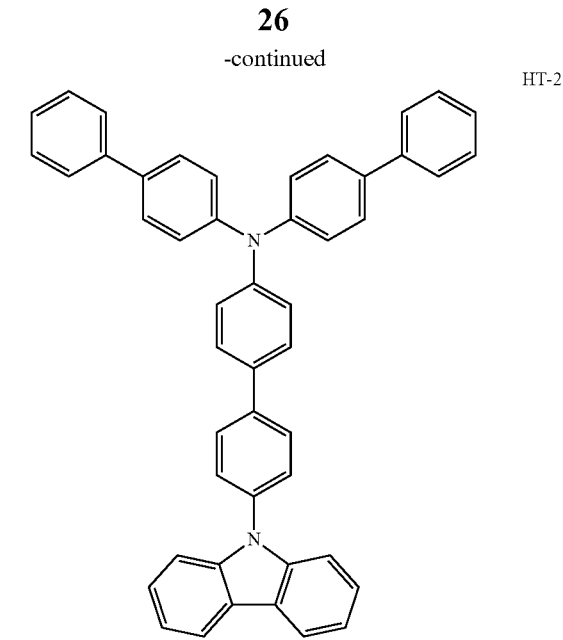

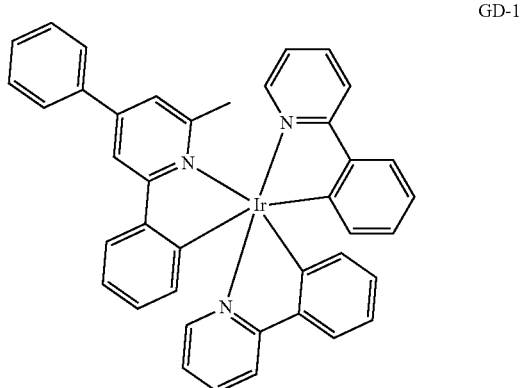

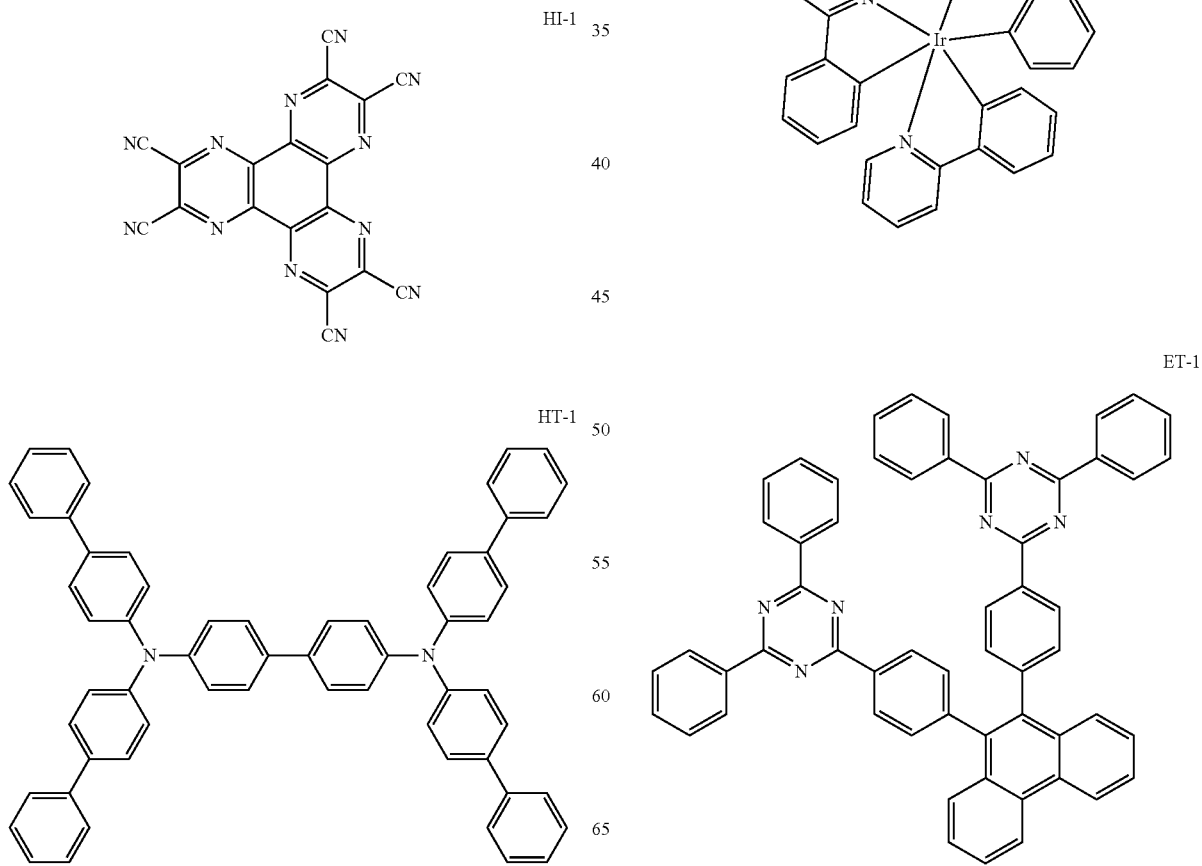

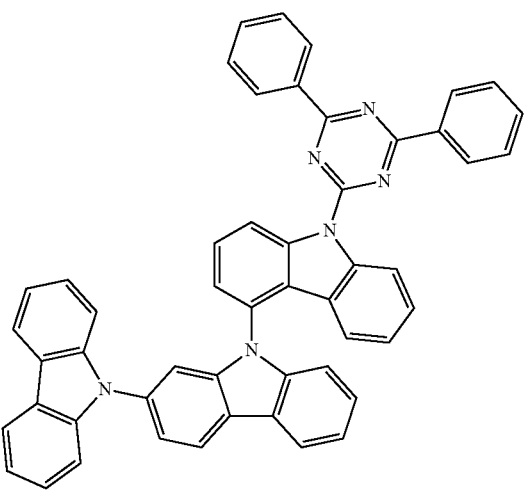

compound C

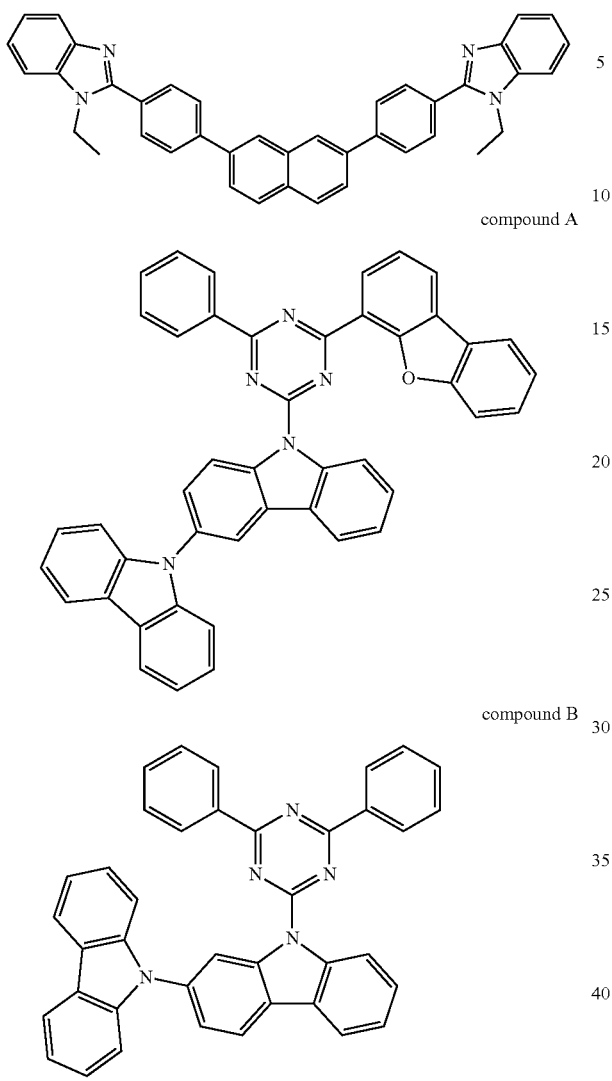

compound A compound B

EXPERIMENTAL EXAMPLE

The voltage, efficiency, color coordinates, and lifetime were measured by applying a current to the organic light emitting devices manufactured in Examples 1 to 3 and Comparative Examples 1 to 3, and the results are shown in Table 1 below.

At this time, T95 means the time required for the luminance to be reduced to 95% when the initial luminance at an optical density of 20 mA/cm² was 100%

TABLE 1

| Category | Host | Voltage (V) (@10 mA/cm²) | Efficiency (%) (@10 mA/cm²) | Color coordinates (x, y) | Lifetime ($T_{95}$, h) (@20 mA/cm²) |
|---|---|---|---|---|---|
| Example 1 | Compound 1 | 3.09 | 62.8 | (0.318, 0.631) | 38.5 |
| Example 2 | Compound 2 | 3.12 | 63.5 | (0.322, 0.630) | 40.3 |
| Example 3 | Compound 3 | 3.20 | 65.1 | (0.321, 0.631) | 50.0 |
| Comparative Example 1 | Compound A | 3.21 | 60.3 | (0.321, 0.630) | 25.0 |
| Comparative Example 2 | Compound B | 3.33 | 59.8 | (0.320, 0.629) | 23.1 |
| Comparative Example 3 | Compound C | 3.59 | 49.1 | (0.339, 0.631) | 5.1 |

As shown in Table 1, it was confirmed that when the compound of the present invention was used, it exhibited excellent effects in terms of voltage, efficiency, and lifetime.

In particular, it was confirmed that the compounds of the present invention exhibited superior properties in terms of efficiency and lifetime due to the difference in the number of substituents and the binding position, as compared with the compounds of the comparative examples.

In the case of the compounds used as the comparative examples, it was confirmed that the lifetime characteristics were significantly reduced as compared with the compounds of the present invention.

[Description of symbols]

| | |
|---|---|
| 1: substrate | 2: anode |
| 3: light emitting layer | 4: cathode |
| 5: hole injection layer | 6: hole transport layer |
| 7: light emitting layer | 8: electron transport layer |

The invention claimed is:

1. A compound of Chemical Formula 1 or 2:

[Chemical Formula 1]

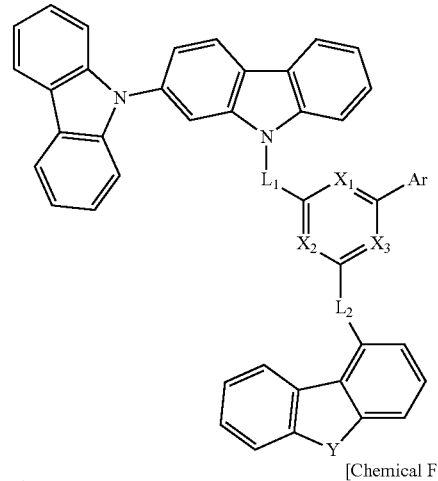

[Chemical Formula 2]

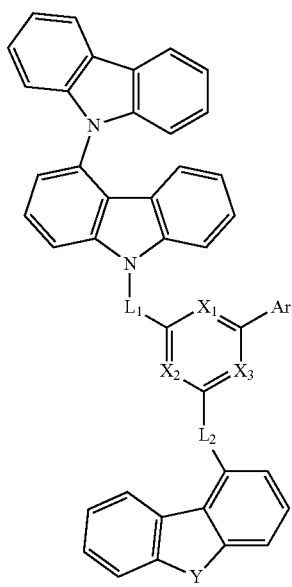

wherein, in Chemical Formulas 1 and 2;

$X_1$ to $X_3$ are N or CH, with the proviso that at least one of $X_1$ to $X_3$ is;

Y is O or S;

$L_1$ and $L_2$ are each independently a single bond or a substituted or unsubstituted $C_{6-60}$ arylene; and Ar is a substituted or unsubstituted $C_{1-60}$ alkyl, a substituted or unsubstituted $C_{1-60}$ haloalkyl, a substituted or unsubstituted $C_{3-60}$ cycloalkyl, a substituted or unsubstituted $C_{6-60}$ aryl, or a substituted or unsubstituted $C_{2-60}$ heteroaryl containing one to three heteroatoms selected from the group consisting of N, O, and S.

2. The compound according to claim 1, wherein:

each of $X_1$, $X_2$ and to $X_3$ is N.

3. The compound according to claim 1, wherein:

$L_1$ and $Y_2$ are each independently a single bond, phenylene, biphenylylene, or terphenylylene.

4. The compound according to claim 1, wherein:

Ar is phenyl or biphenyl.

5. The compound according to claim 1, wherein:

the compound is any one of the following Chemical Formulas 1-1, 1-2, 2-1, and 2-2:

[Chemical Formula 1-1]

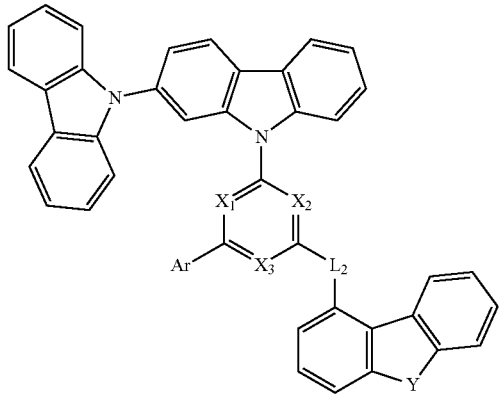

[Chemical Formula 1-2]

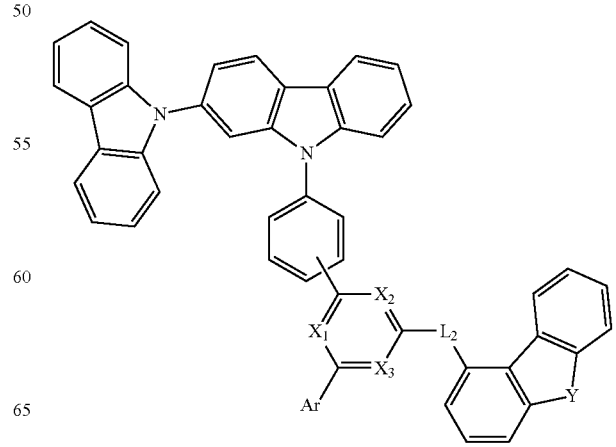

-continued

[Chemical Formula 2-1]

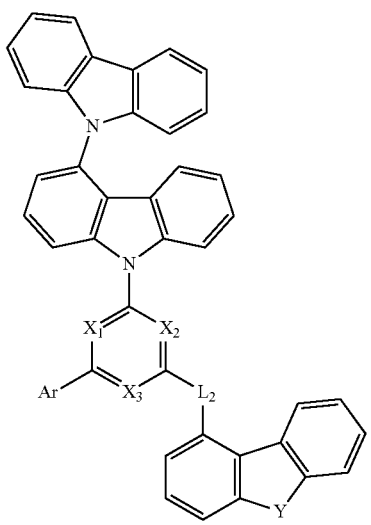

[Chemical Formula 2-2]

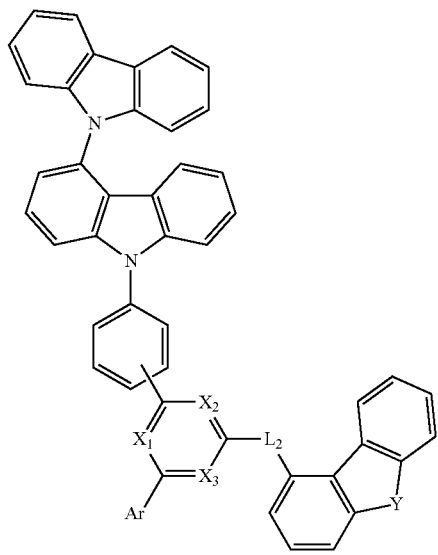

wherein, in Chemical Formulas 1-1, 1-2, 2-1, and 2-2;

$X_1$ to $X_3$ are N or CH, with the proviso that at least one of $X_1$ to $X_3$ is N;

Y is O or S;

$L_2$ is a single bond or a substituted or unsubstituted $C_{6-60}$ arylene; and Ar is a substituted or unsubstituted $C_{1-60}$ alkyl, a substituted or unsubstituted $C_{1-60}$ haloalkyl, a substituted or unsubstituted $C_{3-60}$ cycloalkyl, a substituted or unsubstituted $C_{6-60}$ aryl, or a substituted or unsubstituted $C_{2-60}$ heteroaryl containing one to three heteroatoms selected from the group consisting of N, O, and S.

6. The compound according to claim 1, wherein the compound is any one compound selected from the group consisting of the following compounds:

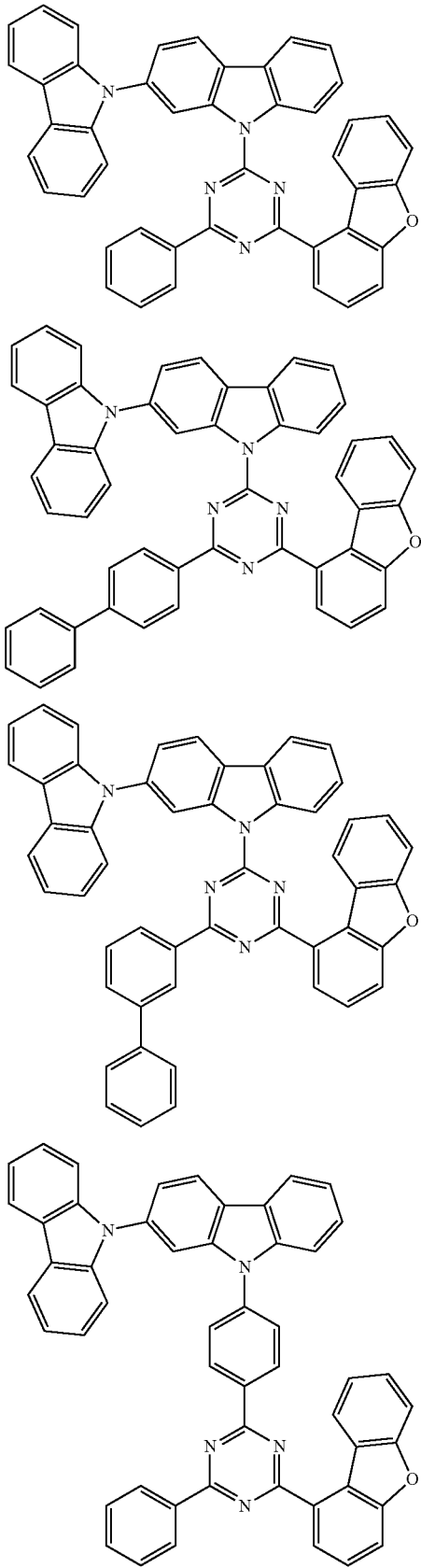

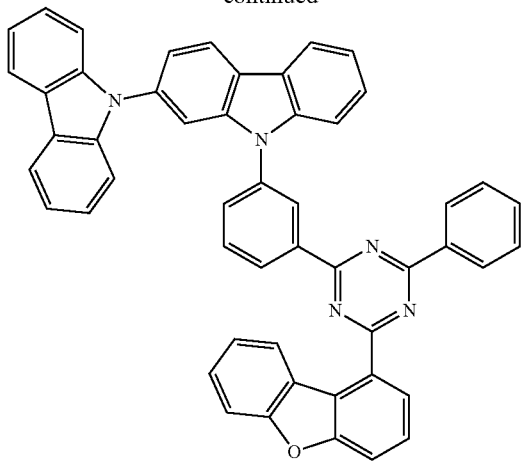
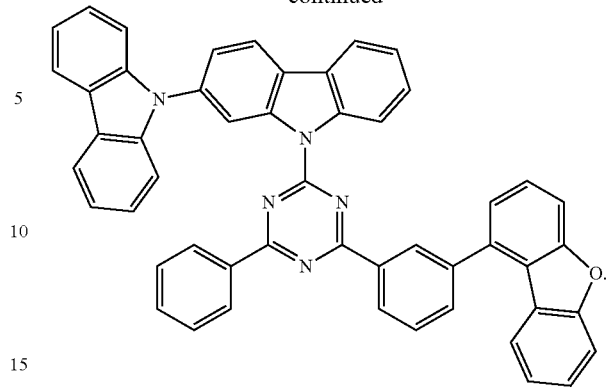

7. An organic light emitting device, comprising:
   a first electrode;
   a second electrode provided opposite to the first electrode; and
   one or more organic material layers provided between the first electrode and the second electrode, wherein one or more one layers of the organic material layers comprise the compound of claim 1.

8. The organic light emitting device according to claim 7, wherein:
   the organic material layer comprising the compound is a light emitting layer.

* * * * *